United States Patent
Lee et al.

(10) Patent No.: US 10,174,239 B2
(45) Date of Patent: Jan. 8, 2019

(54) PROCESS FOR PREVENTING OR MITIGATING BIOFOULING

(71) Applicant: BAKER HUGHES INCORPORATED, Houston, TX (US)

(72) Inventors: Crystal Lee, Sugar Land, TX (US); Joseph E. Penkala, Houston, TX (US); Kenneth G. Wunch, The Woodlands, TX (US)

(73) Assignee: Baker Hughes, a GE company, LLC, Houston, TX (US)

( * ) Notice: Subject to any disclaimer, the term of this patent is extended or adjusted under 35 U.S.C. 154(b) by 223 days.

(21) Appl. No.: 14/520,830

(22) Filed: Oct. 22, 2014

(65) Prior Publication Data

US 2015/0038471 A1    Feb. 5, 2015

Related U.S. Application Data

(63) Continuation-in-part of application No. 13/019,586, filed on Feb. 2, 2011.

(60) Provisional application No. 61/302,604, filed on Feb. 9, 2010.

(51) Int. Cl.
| | |
|---|---|
| A01N 35/02 | (2006.01) |
| A01N 31/04 | (2006.01) |
| A01N 37/10 | (2006.01) |
| A01N 57/20 | (2006.01) |
| C02F 1/50 | (2006.01) |
| C09K 8/22 | (2006.01) |
| C09K 8/60 | (2006.01) |
| C09K 8/68 | (2006.01) |
| A01N 35/04 | (2006.01) |
| C09K 8/524 | (2006.01) |
| C09K 8/04 | (2006.01) |
| C02F 103/10 | (2006.01) |

(52) U.S. Cl.
CPC .............. *C09K 8/605* (2013.01); *A01N 35/04* (2013.01); *C02F 1/50* (2013.01); *C09K 8/04* (2013.01); *C09K 8/524* (2013.01); *C09K 8/68* (2013.01); *C02F 2103/10* (2013.01); *C02F 2303/20* (2013.01)

(58) Field of Classification Search
CPC ........ A01N 57/20; A01N 35/04; A01N 31/08; A01N 33/08; A01N 33/12; A01N 35/02; A01N 41/04; A01N 43/80; A01N 47/48; A01N 59/14; A01N 59/20; C02F 1/50; C02F 2103/10; C02F 2303/20; C09K 8/04; C09K 8/524; C09K 8/605; C09K 8/68

See application file for complete search history.

(56) References Cited

U.S. PATENT DOCUMENTS

| | | | |
|---|---|---|---|
| 4,525,480 A | 6/1985 | Berke et al. | |
| 4,661,518 A | 4/1987 | Lamarre et al. | |
| 4,728,452 A | 3/1988 | Hansen | |
| 5,089,619 A | 2/1992 | Thompson et al. | |
| 5,385,896 A * | 1/1995 | Bryan | A01N 57/34 514/129 |
| 5,560,912 A | 10/1996 | Neeman et al. | |
| 5,719,172 A | 2/1998 | Oppong et al. | |
| 5,738,861 A | 4/1998 | Emerson et al. | |
| 5,854,180 A | 12/1998 | Scherubel et al. | |
| 6,068,056 A | 5/2000 | Frenier et al. | |
| 6,117,364 A | 9/2000 | Vorderbruggen et al. | |
| 6,267,897 B1 * | 7/2001 | Robertson | C02F 5/10 210/764 |
| 6,399,547 B1 | 6/2002 | Frenier et al. | |
| 6,784,168 B1 | 8/2004 | Jones et al. | |
| 7,727,937 B2 | 6/2010 | Pauls et al. | |
| 2004/0102501 A1 * | 5/2004 | Lutz | A01N 35/02 514/389 |
| 2004/0254196 A1 | 12/2004 | Kwon et al. | |
| 2006/0006121 A1 | 1/2006 | Simpson et al. | |
| 2008/0132569 A1 | 6/2008 | Chang et al. | |
| 2009/0191289 A1 | 7/2009 | Lutz et al. | |
| 2009/0258950 A1 | 10/2009 | Knoblauch et al. | |

FOREIGN PATENT DOCUMENTS

EP    0505023 A1    9/1992

OTHER PUBLICATIONS

Seenivasan et al. (BMC Complementary and Alternative Medicine, 2006, 6:39).*
Kawaguchi et al. (JP 08026910, see English translation).*
Melo, L.F., et al., "Biofouling in Water Systems," Exp. Thermal and Fluid Sci. 14: 375-381 (1997).
Chandler, R., "Corrosion Control in Waste Water Systems," 33rd Annual Qld Water Industry Operations Workshop, Indoor Sports Centre, Carrara—Gold Coast, 36-42 (Jun. 3-5, 2008).
Wen, J, et al., "A Green Biocide Enhancer for the Treatment of Sulfate-Reducing Bacteria (SRB) Biofilms on Carbon Steel Surfaces Using Glutaraldehyde," Intrn'l Biodeterioration & Biodegradation 63, 1102-1106 (2009).

(Continued)

*Primary Examiner* — Umamaheswari Ramachandran
(74) *Attorney, Agent, or Firm* — Mossman, Kumar & Tyler, P.C.

(57) ABSTRACT

Biofouling may be prevented or at least mitigated by employing a cinnamaldehyde additive to augment the affect of the conventional biocide. Exemplary cinnamaldehyde additives include, but are not limited to, cinnamaldehyde, cinnamic acid and cinnamyl alcohol. A cinnamaldehyde additive by itself, in some embodiments, may also inhibit biofouling.

13 Claims, 1 Drawing Sheet

(56) References Cited

OTHER PUBLICATIONS

Kull, F.C. et al., "Mixtures of Quaternary Ammonium Compounds and Long-Chain Fatty Acids as Antifungal Agents," Jnl of Applied Microbiology, vol. 9, pp. 538-541 (1961).
Lambert, R.J.W. et al., "Theory of Antimicrobial Combinations: Biocide Mixtures—Synergy or Addition?," Jnl of Applied Microbiology, vol. 94, pp. 747-759 (2003).
Annadorai, Karthik et al., "Effect of THPS on Discharge Water Quality: A Lessons Learned Study," SPE 125785 (2010).
Greene, E. Anne, et al.; "Synergistic Inhibition of Microbial Sulfide Production by Combinations of the Metabolic Inhibitor Nitrite and Biocides", Applied and Environmental Microbiology, Dec. 2006, vol. 72, No. 12, 7897-7901.

\* cited by examiner

PROCESS FOR PREVENTING OR MITIGATING BIOFOULING

CROSS REFERENCE TO RELATED APPLICATION

This application is a continuation-in-part patent application from U.S. patent application Ser. No. 13/019,586 field Feb. 2, 2011, which in turn claims priority from the U.S. Provisional Patent Application Ser. No. 61/302,604 filed Feb. 9, 2010; and which applications are incorporated herein by reference in their entireties.

TECHNICAL BACKGROUND

Technical Field

The present invention relates in one non-limiting embodiment to methods and compositions for inhibiting bacterial and/or algal growth in fluids and/or surfaces, and in another non-restrictive version relates to methods and compositions for inhibiting bacterial and/or algal growth in fluids and/or surfaces using a synergistic biocidal blend of two or more components.

Background of the Art

Throughout the world, there are many different types of industrial water systems. Industrial water systems include water used for cooling and/or energy generation. Biofouling can occur even in industrial water systems treated with the best water treatment programs currently available. For purposes of this patent application, "biofouling" is defined as "the deposition of a biological material on or near a surface in contact with industrial water and/or any diminution of system efficiency due to the accumulation of a biological material within an industrial system that employs industrial water".

If industrial water systems are not treated for microbial fouling control, then they may become subject to heavy biofouling. Such fouling may have a negative impact on an industrial water system and resultant negative economic consequences on the processes utilizing them.

In addition to industrial water systems, biofouling may be a substantial problem in the exploration for and production of oil and gas. Aqueous fluids including but not limited to drilling fluids, production fluids, formation fluids, and the like maybe subject to biofouling. Systems such as these may be referred to as "upstream", as in upstream of a refinery.

Sources of bacterial microorganisms that may cause biofouling in industrial water systems are numerous and may include, but are not limited to, air-borne contamination, water make-up, process leaks and improperly cleaned equipment. Also bacteria that are indigenous to the water used. These microorganisms can establish microbial communities on any wetted or semi-wetted surface of a water system.

SUMMARY

In one non-limiting embodiment there may be provided a process for preventing or mitigating the occurrence of biofouling that includes introducing an effective amount of a biocidal blend comprising a cinnamaldehyde additive and a conventional biocide into an industrial water system, where the biocidal blend decreases the growth of a bacteria selected from the group consisting of acid-producing bacteria, sulfate-reducing bacteria and combinations thereof, such as below expected levels of biofouling. Expected levels of biofouling would be those that would occur without the presence of the biocidal blend. In other words, the growth of bacteria is less than that as compared to an otherwise identical industrial waste system without the biocidal blend.

There may be additionally provided in a different non-restrictive version, a process for preventing or mitigating the occurrence of biofouling comprising introducing from about 50 ppm to about 1000 ppm of a biocidal blend comprising a cinnamaldehyde additive and tetrakis (hydroxymethyl) phosphonium sulfate (THPS) into an industrial water system, where the biocidal blend decreases the growth of a bacteria selected from the group consisting of acid-producing bacteria, sulfate-reducing bacteria and combinations thereof, such as below expected levels of biofouling.

DESCRIPTION OF THE PREFERRED EMBODIMENTS

Figure 1:
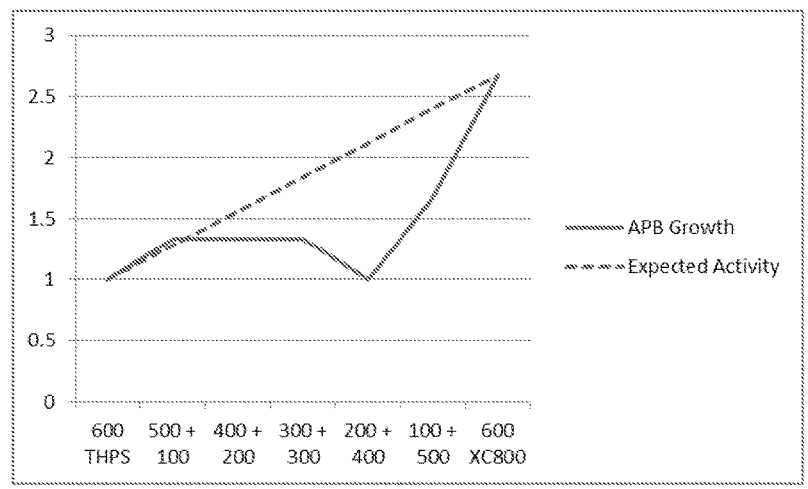
FIG. 1 is a graph of acid-producing bacteria (APB) growth for various blends with different biocidal blends having varying amounts of a cinnamaldehyde additive and a conventional biocide showing expected activity and measured activity.

For the purposes of this application, the term "industrial water systems" also includes fluids associated with the exploration for and production of oil and gas. Industrial water systems include, but are not limited to cooling water, especially those systems that include cooling towers; industrial cleaning processes; and process water preparation systems. In the case of these latter systems, examples could include process water makeup systems for the production of paper, sugar, chemicals, and for use in mining operations.

Exemplary industrial water systems in the field of exploration for and production of oil and gas include aqueous drilling fluids, fluids used for secondary and tertiary recovery, fracture fluids, and the like. Even some "oil-based" fluids have sufficient water to be subject to biofouling and may be treated according to some embodiments of the methods of the disclosure.

Biofouling of industrial water systems may occur utilizing at least two different mechanisms. One of these mechanisms is the generation of biofilms. Biofilms are produced when bacterial colonies develop on the surfaces of the industrial water systems. For example, in a cooling tower biofilms may be developed on the sides of the tower or within the piping inside the tower.

In an oil field, biofilms may occur on the surfaces of drilling equipment, pipelines, secondary equipment such as desalters, and even on the surfaces of the geological formation itself. Exopolymeric substances secreted from microorganisms aid in the formation of biofilms as the microbial communities develop on the surface. These biofilms are complex ecosystems that establish a means for concentrating nutrients and offer protection for growth.

Although they are a problem in themselves, biofilms may cause other problems as well. Biofilms can accelerate scale, corrosion, and other fouling processes. Not only do biofilms contribute to reduction of system efficiencies, but they also provide an excellent environment for microbial proliferation that can include pathogenic bacteria.

The second mechanism is the mass accumulation of biological materials. Biological masses can block pipes and restrict the porosity of the geological formations producing oil and gas. Pipelines and secondary equipment can also be subjected to a restricted flow condition.

Two problematic types of bacteria are sulfate-reducing bacteria (SRB) and acid-producing bacteria (APB). SRB are those bacteria that can obtain energy by oxidizing organic compounds or molecular hydrogen (H2) while reducing sulfate ($SO_4^{2-}$) to hydrogen sulfide ($H_2S$). In a sense, these organisms "breathe" sulfate rather than oxygen in a form of anaerobic respiration. APB are bacteria that produce organic acid products when growing under reductive conditions utilizing organic compounds.

Several factors may contribute to the problem of biofouling and govern its extent. Water temperature; water pH; organic and inorganic nutrients, growth conditions such as aerobic or anaerobic conditions, and in some cases the presence or absence of sunlight, etc. can, in some embodiments, play an important role. These factors may also help in elucidating what types of microorganisms might be present in the water system.

Many different approaches are utilized for the control of biological fouling in industrial processes. The most commonly used method is the application of biocidal compounds to the process waters. The biocides applied may be oxidizing or non-oxidizing in nature. Oxidizing biocides such as chlorine gas, hypochlorous acid, bromine derived biocides, and other oxidizing biocides are widely used in the treatment of industrial water systems.

For example, in one embodiment the conventional biocide may be a halogen-based biocide which readily oxidizes in aqueous solution. In this embodiment, the conventional biocide may release hypochlorous acid into the aqueous solution which may quickly convert to hypobromous acid. Hypobromous acid may be an effective biocide when the system pH is above 7.5, and when nitrogen-based contaminants/odorants (i.e., ammonia/amines) are present.

In another embodiment, the conventional biocide may include trichloroisocyanuric acid or a derivative thereof. In a further embodiment, the biocide may include sodium dichloro-s-triazinetrione (trichloroisocyanuric acid) and sodium bromide.

Conventional biocides, in some embodiments, may include, but are not limited to, isothiazolone, bleaches, and hydantoins. In an example of such an embodiment, the conventional biocide comprises a stabilized halogen compound including stabilized bromine, fluorine, iodine, and chlorine. Other chlorine release compounds, such as chlorinated isocyanurates, hypochlorites, and chlorinated hydantoins may be used with still other embodiments.

Quaternary ammonium compounds are one class of primarily non-oxidizing conventional biocides. These are cationic surface active chemicals which may be effective against algae and bacteria at alkaline pH. These may include, for example, azole materials, including triazoles and imidazoles. Also included in this class are benzalkonium chloride or carbonate; didecyldimethylammonium chloride; tebuconazole; and propiconazole.

The biocide blends described herein may include conventional biocides that exhibit a synergistic effect when added to a fluid stream with a peracetic acid. Examples of such suitable non-oxidizing conventional biocides include benzisothiazolin, carbonimidic dibromide, 1,4-Bis(bromoacetoxy)-2-butene and β-bromo-β-nitrostyrene.

A group of specialized dithiocarbamates, as disclosed by U.S. Pat. No. 5,089,619, which is incorporated herein by reference in its entirety, may also be used as the conventional biocide in some embodiments of the disclosure.

Another group of conventional biocides which may be used in certain embodiments of the disclosure include, but are not necessarily limited to, formaldehyde, p-formaldehyde, and glutaraldehyde. Hydroxyalkylaminoalkanols, e.g. 2-hydroxymethylamino methanol, thiocarbamates, thiocyanates, isothiazolones and the like may be used with some embodiments.

Still another group of suitable biocides include, but are not necessarily limited to, isothiazolin-3-ones such as 2-methyl-4-isothiazolin-3-one, 2 ethyl-4-isothiazolin-3-one, 2-propyl-4-isothiazolin-3-one, 2-butyl-4-isothiazolin-3-one, 2-amyl-4-isothiazolin-3-one, 5-chloro-2-methyl-4-isothiazolin-3-one, 5-bromo-2-methyl-4-isothiazolin-3-one, 5-iodo-2-methyl-4-isothiazolin-3-one, 5-chloro-2-butyl-4-isothiazolin-3-one, 5-bromo-2-ethyl-4-isothiazolin-3-one, 5-iodo-2-amyl-4-isothiazolin-3-one and similar analogs and homologs within the genus.

Complexed biocidal metals may be used as conventional biocides in some embodiments of the disclosure. For example, in the case of copper, suitable relatively insoluble material reactive with complexing agents include, but are not necessarily limited to, cuprous oxide, cupric oxide, copper hydroxide, copper carbonate, copper basic carbonate, copper oxychloride, copper-8-hydroxyquinolate, copper dimethyl dithiocarbamate, copper omadine, copper borate, copper metal byproducts, copper sulfate, copper fluoroborate, copper fluoride, copper formate, copper acetate, copper bromide, copper iodide, copper basic phosphate, copper basic phosphor-sulfate, copper basic nitrate, combinations of these, and the like. Copper basic carbonate, which may be represented by the simplified formula $Cu(OH)_2$—$CuCO_3$), is an example of one source of relatively insoluble copper.

Still other conventional biocides may be used with embodiments of the methods described herein. Exemplary biocides include, but are not limited to, metaborate, sodium dodecylbenzene sulphonate, sodium benzoate, thione, bromonitropropanediol, bromohydroxyacetophenone, dibromodicyanobutane, sodium orthophenylphenate, dodecylguanidine hydrochloride, oxazolidines, adamantanes, dibromonitrilopropionamide, tetrakis hydroxymethyl phosphonium sulfate (THPS), and chloromethylphenol. Any conventional biocide, known or unknown or to be discovered, may be used with certain embodiments of the disclosure.

In addition to biocides, the cinnamaldehyde additives of the disclosure may be used with inert synergistic components. The inert synergistic components are compounds that by themselves do not act as a potent biocide, but may be combined synergistically with cinnamaldehyde additives to form an effective biocide. Examples of inert synergistic components useful with the disclosure include but are not limited to sodium nitrite, sodium molybdate, and anthraquinone. These compounds may be used in the same ratios as the conventional biocides.

The biocide compositions of the methods described herein may include a cinnamaldehyde additive. These compounds may have the general formula (I):

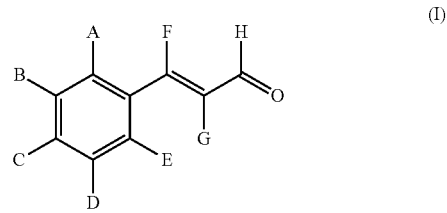

(I)

where A-E are independently selected from a group consisting of hydrogen, halides, alkyl, alkoxy, amino, nitro and hydroxyl and F and G are independently selected from a group consisting of hydrogen, halides and alkyl. In an alternative embodiment, at some low pH conditions, defined in this context as a pH below 7, the cinnamaldehyde additives may be in the form of an acetal or a hemiacetal having the general formula:

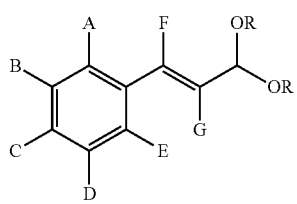

wherein A-E are independently selected from a group consisting of hydrogen, halides, alkyl, alkoxy, amino, nitro and hydroxyl, and F and G are independently selected from a group consisting of hydrogen, halides and alkyl. In this embodiment, the R is selected from the group consisting of hydrogen, alkyl, alkaline metal cation and alkaline earth cation.

More specifically, the cinnamaldehyde additive may, in some embodiments, be selected from the group of compounds represented by the general formula:

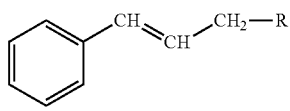

wherein R is a hydroxyl alkyl, carboxylic acid group, or an aldehyde group. The R groups may also include amino and nitro groups. Exemplary compounds include, but are not limited to:

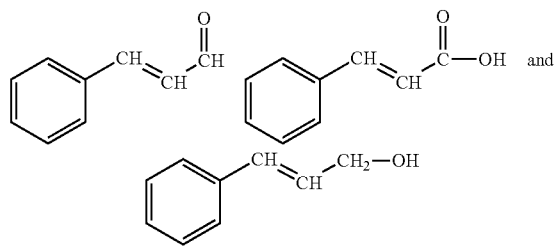

Other compounds that may be used in certain embodiments of the disclosure include, but are not limited to cinnamyl acetate, 3-phenylpropionaldehyde, 2-bromocinnamaldehyde, phenyl propiolic aldehyde, benzalacetone, ethyl cinnamate, 4-chlorocinnamaic acid, 4-nitrocinnamaic acid, and 4 aminocinnamic acid.

Cinnamaldehyde may be extracted from the dried aromatic inner bark of certain tropical Asian trees in the genus *Cinnamomum*, especially *C. verum* and *C. loureirii*. It may also be produced synthetically. For the purposes of this application, the cinnamaldehyde additives of the method described herein may also include other compounds extracted from biological sources (or their synthetic analogs): including vanillin (extracted from *vanilla* beans; genus *Vanilla*, especially *V. planifolia*), eugenol (extracted from the buds of cloves; *Syzygium aromaticum*), and capsaicin (extracted from hot peppers; genus *Capsicum*, especially the species *C. annuum* and *C. frutescens*).

The cinnamaldehyde additives of the disclosure may combine with conventional biocides to produce synergistic improvement to the ability of a conventional biocide to mitigate the formation of APB, SRB and other forms of biofouling organisms. In some embodiments, the weight ratio of conventional biocide to cinnamaldehyde additive may be from about 1:10 to about 1:1. In other embodiments the ratio may be from about 1:8 to about 1:2. The still other embodiments the ratio may be from about 1:5 to about 1:3. In another non-limiting embodiment the volume ratio of cinnamaldehyde additive to conventional biocide at 50 wt % dilution in the biocidal blend ranges from 1:5 to about 5:1. For the prevention or mitigation of APB growth, the volume ratio of cinnamaldehyde additive to conventional biocide at 50 wt % dilution in the biocidal blend ranges from 1:5 to about 4:1.

While the cinnamaldehyde additives of the method may be synergistically combined with other types of compounds, in some embodiments the cinnamaldehyde additives added by themselves may be useful in preventing or mitigating biofouling. The advantages of using a cinnamaldehyde additive alone, that is without neither a conventional biocide nor a synergistic component, are significant. For example, one need not worry about undesirable interactions between the cinnamaldehyde additive and a synergistic or other biocidal component.

Since the cinnamaldehyde additives of the method may be used with many types of conventional biocides, one of ordinary skill in the art employing an embodiment of the method of the disclosure may be required to determine the best ratio of cinnamaldehyde additive to conventional biocide, as well as optimal dosage for their application. Those of ordinary skill in the art well know how to do this.

The biocide compositions of the disclosure may additionally include other compounds and compositions. For example, the biocide compositions of the disclosure may include dispersants, solubilizers, stabilizers, winterizers (e.g. additives such as methanol which may lower the freezing point of the product) and the like.

The compositions of the disclosure may be prepared using any method known to be useful to those of ordinary skill in the art of preparing such compositions. In one embodiment, the cinnamaldehyde additive and the conventional biocide are admixed prior to shipping to a consumer. In another embodiment, where the conventional biocide and a cinnamaldehyde additive are not compatible, the composition may be sent as two components and admixed immediately prior to use.

While the compositions and methods of the disclosure are directed to their use as biocides, in some embodiments, they are directed primarily at use as a bactericide. In some embodiments, these compositions and methods are specifically not directed at use as a fungicide. In some applications they are also not intended for use on crops or in potable water.

In addition to being effective as a biocide, the cinnamaldehyde additives may also be employed in oilfield operations to treat completion fluids and production fluids. For the purposes of this application, a completion fluid is a fluid employed downhole to finish or "complete" an oil well to enable it to begin producing "production fluid." These fluids are typically low-solids fluid or drilling mud that are selected for their ability to control formation pressure and minimize formation damage. "Production fluid" is the fluid that taken from the formation and typically includes brine, natural gas, and crude oil; as well as the other components recovered from an underground formation.

Cinnamaldehyde additives of the methods described herein may be used for dispersing biofilms, and stabilizing compositions including gels, friction reducers, and completions fluids. Gels are used to transport proppants during well stimulation. Gels may comprise aqueous solutions gelled by polysaccharides (in crosslinked or uncrosslinked form) and viscoelastic surfactants (VES). These gels are subject to breaking down and thereby failing to perform their desired function. The cinnamaldehyde additives of the methods described herein may be employed to extend the life and/or improve the function of such gels.

During an oil well stimulation project a fluid, usually water, may be injected/pumped into an oil well very rapidly to among other things, fracture part of a geological formation. The biocidal blend and/or the cinnamaldehyde additives of the methods described herein may be employed to reduce the friction of the fluid injection by extending the life and/or improve the function of conventionally applied friction reducing compounds.

Biofilms may still be a problem downhole even after the living part of the film has expired. The cinnamaldehyde additives of the methods described herein may be employed downhole to disperse such films. These additives may, in some embodiments, be effective in causing such films to release from their substrates and sometimes even further disperse to reduce subsequent particle size after release.

Stabilization can, in some embodiments, mean to cause at two components to remain in a single phase. The cinnamaldehyde additives of the methods described herein can be employed to stabilize by compatibilizing compositions that might otherwise phase out or separate from the fluid in which they are employed. For example, these additives may be employed in the case of production fluid to compatibilize the hydrophobic and hydrophilic components of completion fluids so that they remain in a single phase. They may be further employed to compatibilize a friction reducer with production fluid or even a separated crude oil stream.

The amount of the biocidal blend added to the industrial water system may range from about 50 ppm independently to about 1000 ppm; alternatively from about 75 ppm independently to about 900 ppm; in a non-limiting embodiment from about 100 ppm independently to about 800 ppm, and in a different non-restrictive embodiment from about 150 ppm independently to about 700 ppm. When used with respect to a proportion range, the word "independently" means that any lower threshold may be combined with any upper threshold to give a suitable alternate proportion range.

The following Examples are provided to simply further illustrate the invention and should not necessarily be used to limit the scope of the invention.

EXAMPLES

The following examples are provided to illustrate the present invention. The examples are not intended to limit the scope of the present invention and they should not be so interpreted. Amounts are in weight parts or weight percentages unless otherwise indicated.

Example 1

Water samples containing biofouling bacteria, in this particular case, sulfate-reducing bacteria (SRB), were used to test for synergism of cinnamaldehyde with tetrakis hydroxymethyl phosphonium sulfate (THPS). The samples were treated with different concentrations of THPS in combination with different concentrations of cinnamaldehyde and incubated for 3 hours. Following the treatment, an aliquot of each sample was serially diluted (10-fold dilutions) into culture media for SRB to enumerate the survivors according to NACE TMO 194-2004. The results are presented in Table 1 below:

TABLE 1

| THPS Concentration (ppm) | Cinnamaldehyde Concentration (ppm) | SRB Surviving Treatment (SRB/ml) |
|---|---|---|
| 0 | 0 | $\geq 10^{10}$ |
| 50 | 0 | $\geq 10^{10}$ |
| 100 | 0 | $\geq 10^{10}$ |
| 250 | 0 | $10^{5}$ |
| 0 | 25 | $\geq 10^{10}$ |
| 50 | 25 | $\geq 10^{10}$ |
| 100 | 25 | $\geq 10^{10}$ |
| 250 | 25 | $10^{4}$ |
| 0 | 50 | $\geq 10^{10}$ |
| 50 | 50 | $\geq 10^{10}$ |
| 100 | 50 | $10^{5}$ |
| 250 | 50 | $10^{2}$ |

This test clearly shows that even at very low concentrations, cinnamaldehyde improves the ability of THPS to inhibit the growth of sulfate reducing bacteria.

Example 2

A sample of a bacterial-fouled water was taken from an oil production site and used as a culture base for testing of cinnamaldehyde as a bactericide. The culture was introduced into a synthetic brine (similar to that used for oilfield operations) and turbidity was measure at 600 nm after 24 hours. The results are shown below in Table 2:

TABLE 2

| Cinnamaldehyde Concentration (ppm) | Turbidity |
|---|---|
| 0 | 2.098 |
| 50 | 1.854 |
| 125 | 0.973 |
| 250 | 0.175 |
| 375 | 0.103 |
| 500 | 0.113 |

Example 3

Various biocidal blends with only 50% THPS, only XC800, and different mixtures were tested, along with a control, at preventing or mitigating APB growth. The media was seawater with 3% total dissolved solids (TDS). Contact times were 20 hours and the reaction volume was 50 ml, using 8 bottles per dilution series string. APB growth was measured from 0 to 4 in logarithmic units. XC800 is a cinnamaldehyde additive, specifically cinnamaldehyde, a surfactant, and a glycol ether as a solvent.

The results are presented in Table 3 and graphed in FIG. 1. In FIG. 1, it is expected that the mitigation of APB growth would generally follow a straight line (dashed in FIG. 1) from 600 ppm THPS (50%) to 600 ppm XC800. Surprisingly and unexpectedly, it was discovered that when THPS and XC800 were used together, particularly in ratios of 400 ppm/200 ppm to 100 ppm/500 ppm, APB growth was well below the expected activity curve.

TABLE 3

Mitigation of APB with THPS and Cinnamaldehyde

| Sample | ppm Product | APB | | |
|---|---|---|---|---|
| Control | 0 | 4 | 4 | 4 |
| 50% THPS only | 600 | 1 | 1 | 1 |
| 50% THPS + XC800 | 500 + 100 | 1 | 1 | 2 |
| 50% THPS + XC800 | 400 + 200 | 1 | 1 | 2 |
| 50% THPS + XC800 | 300 + 300 | 1 | 1 | 2 |
| 50% THPS + XC800 | 200 + 400 | 1 | 1 | 1 |
| 50% THPS + XC800 | 100 + 500 | 2 | 1 | 2 |
| XC800 only | 600 | 2 | 3 | 3 |

Example 4

Various biocidal blends with only 50% THPS, only XC800, and different mixtures were tested, along with a control, at preventing or mitigating SRB growth. Again, the media was seawater with 3% total dissolved solids (TDS). Contact times were 20 hours and the reaction volume was 50 ml, using 8 bottles per string. SPB growth was measured from 0 to 4 in in logarithmic units.

Figure 2:
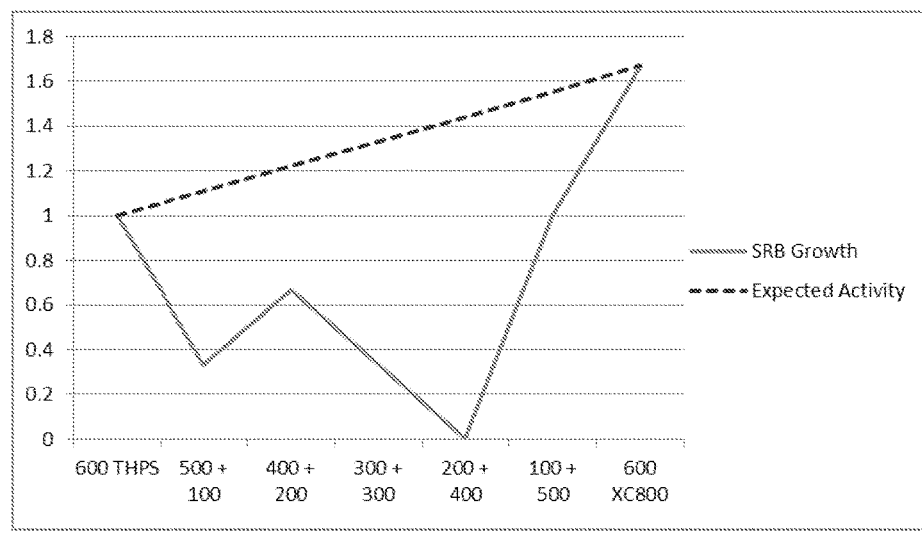
FIG. 2 is a graph of sulfate-reducing bacteria (SRB) growth for various blends with different biocidal blends having varying amounts of a cinnamaldehyde additive and a conventional biocide showing expected activity and measured activity

The results are graphed in FIG. 2. In FIG. 2, it is expected that the mitigation of SRB growth would generally follow a straight line (dashed in FIG. 2) from 600 ppm THPS (50%) to 600 ppm XC800. Surprisingly and unexpectedly, it was discovered that when THPS and XC800 were used together, particularly in ratios of 500 ppm/100 ppm to 100 ppm/500 ppm, SRB growth was well below the expected activity curve.

In the foregoing specification, the invention has been described with reference to specific embodiments thereof, and has been demonstrated as effective in providing methods and compositions for preventing or mitigating the occurrence of biofouling, particularly the preventing or mitigating the growth of APB and/or SRB. However, it will be evident that various modifications and changes can be made thereto without departing from the broader scope of the invention as set forth in the appended claims. Accordingly, the specification is to be regarded in an illustrative rather than a restrictive sense. For example, the number and kind of cinnamaldehyde additives, conventional biocides, industrial water systems, proportions thereof, and other components falling within the claimed parameters, but not specifically identified or tried in a particular composition or method, are expected to be within the scope of this invention. Further, it is expected that the methods, sequences of additions, proportions, identities of components may change somewhat from one application to another and still accomplish the stated purposes and goals of the methods described herein. For example, the methods may use different components, fluids, component combinations, different fluid and component proportions and additional or different steps than those described and exemplified herein.

The words "comprising" and "comprises" as used throughout the claims is to be interpreted as "including but not limited to".

The present invention may suitably comprise, consist or consist essentially of the elements disclosed and may be practiced in the absence of an element not disclosed. For instance, there may be provided a process for preventing or mitigating the occurrence of biofouling that consists essentially of or consists of introducing an effective amount of a biocidal blend comprising a cinnamaldehyde additive and a conventional biocide into an industrial water system, where the biocidal blend decreases the growth of a bacterial selected from the group consisting of acid-producing bacteria, sulfate-reducing bacteria and combinations thereof, such as below expected levels of biofouling.

There may be further provided in a different non-limiting embodiment a process for preventing or mitigating the occurrence of biofouling consisting essentially of or consisting of introducing from about 50 ppm to about 1000 ppm of a biocidal blend comprising a cinnamaldehyde additive and tetrakis (hydroxymethyl) phosphonium sulfate (THPS) into an industrial water system, where the biocidal blend decreases the growth of a bacterial selected from the group consisting of acid-producing bacteria, sulfate-reducing bacteria and combinations thereof, such as below expected levels of biofouling.

What is claimed is:

1. A process for mitigating the occurrence of biofouling comprising introducing from about 50 ppm to about 1000 ppm of a biocidal blend comprising cinnamaldehyde and tetrakis (hydroxymethyl) phosphonium sulfate (THPS) into an industrial water system, where the biocidal blend decreases the growth of a bacteria selected from the group consisting of acid-producing bacteria, sulfate-reducing bacteria and combinations thereof, where the growth of bacteria is equal to or less than expected compared to the use of the cinnamaldehyde used alone or THPS used alone in the same amount and the expected activity curve between the two, where
the industrial water system is selected from water systems used in the field of exploration for and production of oil and gas selected from the group consisting of:
aqueous drilling fluids,
fluids used for secondary and tertiary recovery, and
fracture fluids;
where the volume ratio of cinnamaldehyde to THPS at 50 wt % dilution in the biocidal blend ranges from 1:5 to about 5:1.

2. The process of claim 1 where:
when the bacteria are acid-producing bacteria (APB), the weight ratio of THPS:cinnamaldehyde ranges from 50:50 to 10:50; and
when the bacteria are sulfate-reducing bacteria (SRB), the weight ratio of THPS:cinnamaldehyde ranges from 50:10 to 10:50.

3. The process of claim 1 where the cinnamaldehyde additionally disperses expired biofilms.

4. A process for mitigating the occurrence of biofouling comprising introducing from about 50 ppm to about 1000 ppm of a biocidal blend comprising cinnamaldehyde and tetrakis (hydroxymethyl) phosphonium sulfate (THPS) into an industrial water system, where the biocidal blend decreases the growth of a bacteria selected from the group consisting of acid-producing bacteria (APB), sulfate-reducing bacteria (SRB) and combinations thereof, where the growth of bacteria is equal to or less than expected compared to the use of the cinnamaldehyde used alone or THPS used alone in the same amount and the expected activity curve between the two, where
the industrial water system is selected from water systems used in the field of exploration for and production of oil and gas selected from the group consisting of:
aqueous drilling fluids,
fluids used for secondary and tertiary recovery, and
fracture fluids; and when the bacteria are acid-producing bacteria (APB), the weight ratio of THPS at 50 wt % dilution:cinnamaldehyde ranges from 4:1 to 1:5; and when the bacteria are sulfate-reducing bacteria (SRB), the weight ratio of THPS at 50 wt % dilution:cinnamaldehyde ranges from 5:1 to 1:5.

5. The process of claim 4 where the cinnamaldehyde additionally disperses expired biofilms.

6. A process for mitigating the occurrence of biofouling consisting of introducing from about 50 ppm to about 1000 ppm of a biocidal blend consisting of cinnamaldehyde and tetrakis (hydroxymethyl) phosphonium sulfate (THPS) into an industrial water system, where the biocidal blend decreases the growth of a bacteria selected from the group consisting of acid-producing bacteria (APB), sulfate-reducing bacteria (SRB) and combinations thereof, where the growth of bacteria is less than expected compared to the use of the cinnamaldehyde used alone or THPS used alone in the same amount and the expected activity curve between the two, where the industrial water system is selected from water systems used in the field of exploration for and production of oil and gas selected from the group consisting of:
aqueous drilling fluids,
fluids used for secondary and tertiary recovery, and fracture fluids; and when the bacteria are acid-producing bacteria (APB), the weight ratio of THPS at 50 wt % dilution:cinnamaldehyde ranges from 4:1 to 1:5; and when the bacteria are sulfate-reducing bacteria (SRB), the weight ratio of THPS at 50 wt % dilution:cinnamaldehyde ranges from 5:1 to 1:5.

7. The process of claim 6 where the cinnamaldehyde additive additionally disperses expired biofilms.

8. The process of claim 4 where the amount of cinnamaldehyde ranges from 25 to 500 ppm.

9. The process of claim 4 where:

when the bacteria are APB, the amount of cinnamaldehyde ranges from 100 to 400 ppm; and when the bacteria are SRB, the amount of cinnamaldehyde ranges from 25 to 500 ppm.

10. The process of claim 9 where the bacteria are SRB and the amount of cinnamaldehyde ranges from 25 to 50 ppm.

11. The process of claim 6 where the amount of cinnamaldehyde ranges from 25 to 500 ppm.

12. The process of claim 6 where:

when the bacteria are APB, the amount of cinnamaldehyde ranges from 100 to 400 ppm; and when the bacteria are SRB, the amount of cinnamaldehyde ranges from 25 to 500 ppm.

13. The process of claim 12 where the bacteria are SRB and the amount of cinnamaldehyde ranges from 25 to 50 ppm.

* * * * *